United States Patent [19]

Jaffery

[11] Patent Number: 5,153,230
[45] Date of Patent: Oct. 6, 1992

[54] TOPICAL SKIN CREAM COMPOSITION

[75] Inventor: Manzoor H. Jaffery, Stamford, Conn.

[73] Assignee: Perfective Cosmetics, Inc., Stamford, Conn.

[21] Appl. No.: 649,148

[22] Filed: Feb. 1, 1991

Related U.S. Application Data

[63] Continuation of Ser. No. 418,325, Oct. 6, 1989, abandoned.

[51] Int. Cl.⁵ ............................................. A61K 7/48
[52] U.S. Cl. ............................................. 514/847; 514/873
[58] Field of Search ............... 514/846, 847, 725, 784

[56] References Cited

U.S. PATENT DOCUMENTS

| | | | |
|---|---|---|---|
| 4,035,513 | 7/1977 | Kumano | 514/784 |
| 4,124,720 | 11/1978 | Wenmaekers | 514/784 |
| 4,195,077 | 3/1980 | Marsh et al. | 514/784 |
| 4,287,214 | 9/1981 | Van Scott | 514/784 |
| 4,294,852 | 10/1981 | Wildnauer et al. | 514/784 |
| 4,695,452 | 9/1987 | Gannis et al. | 514/725 |

*Primary Examiner*—Dale R. Ore
*Attorney, Agent, or Firm*—Melvin I. Stoltz

[57] ABSTRACT

In a preferred embodiment, a formulation for the treatment of aging skin in which the major active ingredient is glycolic acid in a concentration of from an effective amount up to about 3.5 weight percent. Other active ingredients may be vitamin A palmitate and/or vitamin E acetate. The active ingredients are provided in a moisturizing cream base which has beneficial effects in itself. Preservatives are also provided in the formulation to increase the shelf life thereof.

7 Claims, No Drawings

TOPICAL SKIN CREAM COMPOSITION

This application is a continuation, of application Ser. No. 07/418,325, filed Oct. 6, 1989, now abandoned.

1. Field of the Invention

The present invention relates to preparations for topical application to human skin generally, and, more particularly, to a novel skin cream that is especially useful in the prevention and treatment of aging skin.

2. Background Art

Aging skin is a condition experienced by people as they become older and is characterized by dryness, wrinkling, and the appearance of oldness. As the lifespan of people has increased, the need to keep the skin healthy and youthful-looking has grown in importance. Without care, the skin loses its resiliency and is depleted of its natural oils and moisture.

Recently, Retin-A creams have become available which are intended to address the above condition. While somewhat effective in some cases, the active ingredient, Retin-A, is highly toxic and such creams are available only as prescription drugs. Others products currently being marketed include those containing vitamin A acetate, vitamin A alcohol, and/or proteins and have very little beneficial effect, if any.

Accordingly, it is a principal object of the present invention to provide a formulation for the treatment of aging skin.

It is another object of the invention to provide such a formulation which provides moisturization of the skin.

It is a further object of the invention to provide such a formulation which reduces wrinkling of the skin.

It is an additional object of the invention to provide such a formulation which is highly safe and does not require a prescription for the purchase thereof by consumers.

Other objects of the present invention, as well as particular features and advantages thereof, will be elucidated in, or be apparent from, the following description.

SUMMARY OF THE INVENTION

The present invention accomplishes the above objects, among others, by providing, in a preferred embodiment, a formulation for the treatment of aging skin in which the major active ingredient is glycolic acid in a concentration of from an effective amount up to about 3.5 weight percent. Other active ingredients may be vitamin A palmitate and/or vitamin E acetate. The active ingredients are provided in a moisturizing cream base which has beneficial effects in itself. Preservatives are also provided in the formulation to increase the shelf life thereof.

DETAILED DESCRIPTION OF THE PREFERRED EMBODIMENTS

The following examples of specific embodiments of the invention are for purposes of illustrating the invention and are not intended as limitations thereon.

EXAMPLE

The following formulation has found to be particularly effective in achieving the above objects:

| Constituent | Concentration, wt. % |
| --- | --- |
| Glycolic Acid | 2.1 |
| Vitamin A Palmitate | 1.00 |
| Vitamin E Acetate | 0.5 |
| Cetyl Esters Wax | 8.4 |
| Stearyl Alcohol | 10. |
| Cetyl Alcohol | 4. |
| Glycerin | 10. |
| Methyl Paraben | 0.2 |
| Propyl Paraben | 0.02 |
| Quaternium-15 | 0.1 |
| Sodium Lauryl Sulfate | 2.5 |
| De-ionized Water | Balance |

Glycolic acid is the main active ingredient and may be provided in the formulation as an antiaging agent, which it is believed acts by biosynthesis of collagen, and may be provided in a concentration of from an effective amount up to about 3.5 wt. % and is preferably provided in the range of from about 1.5 wt. % to about 3.2 wt. %. Similar acids, such as fumaric, tartaric, L-aspartic, gluconic, and/or ascorbic may be used with, or in place of, glycolic acid, in effective percentages. Glycolic acid has been found to be particularly efficacious and being a natural product derived from sugarcane, it is much safer than the Retin-A-based products now being marketed. Glycolic acid is compounded in the formulation as a 70-% water solution. The percentages for glycolic acid given above and in the appended claims do not include the water with which the glycolic acid is furnished.

Vitamin A palmitate (retinyl palmitate) may be provided in the formulation as an active ingredient to protect the skin and promote healing and may be provided in a concentration of from an effective amount up to about 5 wt. % and is preferably provided in the range of from about 1 wt. % to about 5 wt. %.

Vitamin E acetate (tocopheryl acetate) may be provided in the formulation as an active ingredient to protect the skin and to promote healing and may be provided in a concentration of from an effective amount up to about 5 wt % and is preferably provided in the range of from about 0.5 wt. % to about 5 wt. %.

The combination of glycolic acid, vitamin A palmitate, and vitamin E acetate has been found to have a unique effect on the skin in smoothing the skin. The mechanism of this effect is not known, but the effects of the combination are visible within one week.

Although a simple solution of glycolic acid in water is effective in treating aging skin, the following ingredients are provided for cosmetic effects and/or to improve the physical consistency of the formulation and to serve as a diluent for the active ingredients:

Cetyl esters wax is synthetically derived and is generally indistinguishable from natural spermaceti wax with regards to composition and properties. It consists of a mixture of esters of 14 to 18 carbon fatty acids and alcohols and may be provided in the formulation as an emollient, or softening agent. Cetyl esters wax may be provided in the formulation in a concentration of from an effective amount up to about 10 wt. % and is preferably provided in the range of from about 5 wt. % to about 9 wt.

Stearyl alcohol may be provided in the formulation as a lubricant and may be provided in a concentration of from an effective amount up to about 15 wt. % and is preferably provided in the range of from about 5 wt. % to about 12 wt. 7%.

Cetyl alcohol may be provided in the formulation as an emulsifying and thickening agent and may be provided in a concentration of from an effective amount up to about 6 wt. % and is preferably provided in the range of from about 2 wt. % to about 5 %.

Glycerin may be provided in the formulation as an emollient and humectant and may be provided in a concentration of from an effective amount up to about 18 wt. % and is preferably provided in the range of from about 2 wt. % to about 12 wt. %.

Cetyl esters wax, stearyl alcohol, cetyl alcohol, and glycerin comprise a moisturizing cream base which makes the active ingredients convenient to apply to the skin and which has beneficial effects in itself. Similar materials may be substituted for these, provided they produce a satisfactory moisturizing cream base. Glycerin is a preferable ingredient as a moisturizer, as it is hygroscopic.

The following three ingredients are provided to improve the shelf life of the formulation:

Methyl paraben may be provided in the formulation as a preservative and may be provided in a concentration of from an effective amount up to about 0.4 wt. % and is preferably provided in the range of from about 0.05 wt. % to about 0.3 wt. %.

Propyl paraben may be provided in the formulation as an antifungal agent and may be provided in a concentration of from an effective amount up to about 0.1 wt. % and is preferably provided in the range of from about 0.02 wt. % to about 0.05 wt. %.

Quaternium-15 may be provided in the formulation as a preservative and may be provided in a concentration of from an effective amount up to about 0.15 wt. % and is preferably provided in the range of from about 0.05 wt. % to about 0.12 wt. %.

Sodium lauryl sulfate may be provided in the formulation as a wetting and emulsifying agent to aid in compounding the formulation and may be provided in a concentration of from an effective amount up to about 1.5 wt. % and is preferably provided in the range of from about 0.5 wt. % to about 1.0 wt. %.

De-ionized water may be provided in the formulation as an inert carrier which acts as a diluent and which also has some moisturizing properties.

It will thus be seen that the objects set forth above, among those made apparent from the preceding description, are efficiently attained and, since certain changes may be made in the above formulation without departing from the scope of the invention, it is intended that all matter contained in the above description shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A topical skin cream composition comprising
   A. between about 1.5% and 3.5% by weight of an acid selected from the group consisting of glycolic acid; fumaric acid; tartaric acid; L-aspartic acid; gluconic acid; and ascorbic acid;
   B. between about 1% and 5% by weight of vitamin A palmitate;
   C. between about 0.5% and 5% by weight of vitamin E acetate; and
   D. a diluent or carrier for the composition comprising one or more compounds selected from the group consisting of emollients, lubricants, emulsifying agents, thickening agents, and humectants.

2. The composition defined in claim 1, wherein said diluent or carrier further comprises at least one compound selected from the group consisting of preservatives, antifungal agents, wetting agents, and emulsifying agents.

3. The composition defined in claim 1, wherein said diluent or carrier comprises
   A. an emollient or softening agent consisting of between about 5% and 9% by weight of cetyl esters wax;
   B. a lubricant consisting of between about 5% and 12% by weight of ceryl alcohol;
   C. an emulsifying or thickening agent comprising between about 2% and 5% by weight of cetyl alcohol; and
   D. an emollient or humectant comprising between about 2% and 12% by weight of glycerin.

4. The composition defined in claim 1, wherein said diluent or carrier comprises
   A. a preservative comprising between about 0.05% and 0.3% by weight of methyl paraben;
   B. an antifungal agent comprising between about 0.02% and 0.5% by weight of propyl paraben;
   C. a preservative comprising between about 0.05% and 0.12% by weight of quaternium-15; and
   D. a wetting or emulsifying agent comprising between about 0.05% and 1% by weight of sodium lauryl sulfate.

5. A topical skin cream composition comprising:
   A. between about 1.5% and 3.5% by weight of glycolic acid;
   B. between about 1% and 5% by weight of vitamin A palmitate;
   C. between about 0.5% and 5% by weight of vitamin E acetate; and
   D. a moisturizing cream base comprising at least one emollient or humectant selected from the group consisting of cetyl esters wax, stearyl alcohol, cetyl alcohol, and glycerin, a preservative selected from the group consisting of methyl paraben and propyl paraben, and sodium lauryl sulfate as an emulsifier; and
   E. water forming the balance.

6. The composition defined in claim 5, wherein said composition comprises
   A. about 2.1% by weight of glycolic acid;
   B. 1% by weight of vitamin A palmitate;
   C. 0.5% by weight of vitamin E acetate;
   D. about 8.4% by weight of cetyl esters wax;
   E. about 10% by weight of stearyl alcohol;
   F. about 4 by weight of cetyl alcohol;
   G. about 10% by weight of glycerin;
   H. about 0.2% by weight of methyl paraben;
   I. about 0.02% by weight of propyl paraben;
   J. about 0.1% by weight of quaternium-15;
   K. about 2.5% by weight of sodium lauryl sulfate; and
   L. de-ionized water forming the balance.

7. A topical skin cream composition comprising:
   A. between about 1.5% and 3.5% by weight of an acid selected from the group consisting of glycolic acid; fumaric acid; tartaric acid; L-aspartic acid; gluconic acid; and ascorbic acid;

B. between about 1% and 5% by weight of vitamin A palmitate;
C. between about 0.5% and 5% by weight of vitamin E acetate;
D. between about 5% and 9% by weight of a wax consisting of a mixture of esters of fatty acids and alcohols having 14 to 18 carbon atoms;
E. between about 5% and 12% by weight of stearyl alcohol;
F. between about 2% and 5% by weight of cetyl alcohol;
G. between about 2% and 12% by weight of glycerine; and
H. de-ionized water forming balance.

* * * * *